US011583210B2

(12) United States Patent
Moore

(10) Patent No.: US 11,583,210 B2
(45) Date of Patent: Feb. 21, 2023

(54) BRACE HAVING INTEGRATED REMOTE PATIENT MONITORING TECHNOLOGY AND METHOD OF USING SAME

(71) Applicant: DJO, LLC, Vista, CA (US)

(72) Inventor: Michael Wayne Moore, Oceanside, CA (US)

(73) Assignee: DJO, LLC, Vista, CA (US)

( * ) Notice: Subject to any disclaimer, the term of this patent is extended or adjusted under 35 U.S.C. 154(b) by 668 days.

(21) Appl. No.: 16/124,988

(22) Filed: Sep. 7, 2018

(65) Prior Publication Data

US 2019/0133497 A1 May 9, 2019

Related U.S. Application Data

(60) Provisional application No. 62/583,168, filed on Nov. 8, 2017, provisional application No. 62/582,863, filed on Nov. 7, 2017.

(51) Int. Cl.
*A61B 5/11* (2006.01)
*A61B 5/107* (2006.01)
(Continued)

(52) U.S. Cl.
CPC .......... *A61B 5/1121* (2013.01); *A61B 5/1073* (2013.01); *A61B 5/4533* (2013.01);
(Continued)

(58) Field of Classification Search
CPC ......... A61B 5/107; A61B 5/1073; A61B 5/11; A61B 5/1113; A61B 5/1114;
(Continued)

(56) References Cited

U.S. PATENT DOCUMENTS 3,121,210 A * 2/1964 Orozco .................. H01C 10/24
338/149
3,849,668 A * 11/1974 Dane ...................... B25J 17/025
307/149
(Continued)

FOREIGN PATENT DOCUMENTS

CN 1344140 A 4/2002
CN 101282698 A 10/2008
(Continued)

OTHER PUBLICATIONS

International Search report dated Dec. 7, 2018, issued in PCT/US2018/050009.
(Continued)

*Primary Examiner* — Michelle J Lee
(74) *Attorney, Agent, or Firm* — Veros Legal Solutions, LLP

(57) ABSTRACT

A brace configured for attachment to a joint of a subject is provided. The brace includes a first arm having a first end and a second end. The brace includes a second arm having a first end and a second end. The brace includes a hinge assembly coupling the first end of the first arm with the first end of the second arm such that the first arm and the second arm are movable to different relative angular orientations. The brace includes a potentiometer coupled to the hinge assembly. A method of monitoring a relative angular orientation of a first arm of a brace relative to a second arm of the brace is also provided. The method includes monitoring an output of a potentiometer coupled to one of the first arm and the second arm.

14 Claims, 11 Drawing Sheets

(51) Int. Cl.
*A61B 5/00* (2006.01)
*A61F 5/01* (2006.01)
*G16H 10/60* (2018.01)
*G16H 40/63* (2018.01)

(52) U.S. Cl.
CPC ............ *A61B 5/4585* (2013.01); *A61F 5/013* (2013.01); *A61F 5/0123* (2013.01); *A61B 5/1071* (2013.01); *A61B 5/112* (2013.01); *A61B 5/1114* (2013.01); *A61B 5/4514* (2013.01); *A61B 5/4523* (2013.01); *A61B 5/6831* (2013.01); *A61B 2505/09* (2013.01); *A61F 2005/0137* (2013.01); *A61H 2201/165* (2013.01); *A61H 2201/501* (2013.01); *A61H 2201/5043* (2013.01); *A61H 2201/5084* (2013.01); *G16H 10/60* (2018.01); *G16H 40/63* (2018.01)

(58) Field of Classification Search
CPC ............ A61B 5/112–1122; A61B 5/45; A61B 5/4504; A61B 5/4514–4538; A61B 5/458; A61B 5/4585; A61B 5/68–6802; A61B 5/6812; A61B 5/6813; A61B 5/6828; A61B 5/683; A61B 5/6831; A61B 5/6835; A61B 2505/00; A61B 2505/09; G16H 10/60; G16H 10/65; G16H 40/60–67; A61H 2201/16; A61H 2201/164–1652; A61H 2201/50; A61H 2201/5007–5015; A61H 2201/5023; A61H 2201/5043; A61H 2201/5046; A61H 2201/5058; A61H 2201/5069; A61H 2201/5084; A61F 5/01–013; A61F 5/0137–0141; A61F 5/058–05875; A61F 2005/0132–0188
See application file for complete search history.

(56) References Cited

U.S. PATENT DOCUMENTS

| | | | |
|---|---|---|---|
| 4,669,302 A * | 6/1987 | Wagner | G09B 23/32 73/818 |
| 5,474,088 A | 12/1995 | Zaharkin et al. | |
| 5,823,975 A | 10/1998 | Stark et al. | |
| 5,935,086 A * | 8/1999 | Beacon | A61B 5/103 600/595 |
| 8,444,564 B2 | 5/2013 | Mahfouz et al. | |
| 8,775,213 B2 | 7/2014 | Hughes et al. | |
| 9,248,040 B2 | 2/2016 | Soderberg et al. | |
| 9,418,571 B2 | 8/2016 | Younger | |
| 9,642,572 B2 | 5/2017 | Mahfouz et al. | |
| 2003/0093021 A1 | 5/2003 | Goffer | |
| 2004/0049140 A1 | 3/2004 | Doty et al. | |
| 2004/0215111 A1 | 10/2004 | Bonutti et al. | |
| 2005/0113652 A1 | 5/2005 | Stark et al. | |
| 2011/0152736 A1 | 6/2011 | Ng | |
| 2011/0257928 A1 * | 10/2011 | Cunningham | G01L 25/006 324/109 |
| 2011/0288611 A1 * | 11/2011 | Lunau | A61N 1/0408 607/51 |
| 2014/0213951 A1 * | 7/2014 | Pietrusisnki | A61H 3/008 602/23 |
| 2015/0057587 A1 | 2/2015 | Walsh et al. | |
| 2015/0302162 A1 | 10/2015 | Hughes et al. | |
| 2016/0008220 A1 | 1/2016 | Greiner et al. | |
| 2016/0128890 A1 * | 5/2016 | LaChappelle | A61H 3/00 623/30 |

FOREIGN PATENT DOCUMENTS

| | | |
|---|---|---|
| CN | 101636142 A | 1/2010 |
| CN | 103379883 A | 10/2013 |
| CN | 104822346 A | 8/2015 |
| EP | 0302148 A1 | 2/1989 |
| JP | 2005517145 A | 6/2005 |
| JP | 2012527314 A | 11/2012 |
| WO | 2019094096 A1 | 9/2018 |
| WO | 2019094096 A1 | 5/2019 |

OTHER PUBLICATIONS

Written Opinion of the ISA dated Dec. 7, 2018, issued in PCT/US2018/050009.

* cited by examiner

BRACE HAVING INTEGRATED REMOTE PATIENT MONITORING TECHNOLOGY AND METHOD OF USING SAME

CROSS-REFERENCE TO RELATED APPLICATIONS

This application claims priority to U.S. Provisional Application No. 62/582,863, filed on Nov. 7, 2017 and U.S. Provisional Application No. 62/583,168, filed on Nov. 8, 2017, the entire contents of which are hereby incorporated by reference.

BACKGROUND

Field of the Disclosure

The present disclosure relates generally to a brace having integrated remote patient monitoring technology and a method of using the same.

Description of the Related Technology

Damaged ligaments, cartilage, and tendons in joints are not an uncommon occurrence, particularly with today's emphasis on physical activity and conditioning. Few injuries interfere with motion more than injuries to the knee. Knee injuries account for approximately 60% of all sports related injuries with nearly half of those injuries occurring to the ACL. ACL injury is most prevalent (1 in 1,750 persons) in patients between the ages of 15 and 45, due in no small measure to their more active lifestyle as well as higher participation in sports. A person who has torn their ACL has a 15 times greater risk of a second ACL injury during the initial 2 months after ACL reconstruction, and risk of ACL injury to the opposite knee is two times that of the restructured knee.

There are four main ligaments which hold the knee together: Anterior Cruciate Ligament (ACL), Posterior Cruciate Ligament (PCL), Medial Collateral Ligament (MCL) and Lateral Collateral Ligament (LCL). There are over 200,000 ACL injuries that occur in the United States annually. Approximately 50% of ACL injuries occur with injuries to other structures of the knee. While less common than an ACL injury, injuries to the PCL account for between 3% to 20% of all knee ligament injuries. The collateral ligaments, MCL and LCL, are responsible for 25% of knee injuries in competitive athletes.

Treatments for ACL and other ligament injuries include surgical and non-surgical options. Braces are employed to promote support and stabilization while ligaments heal. In the case of ACL surgery, graft strength of a new ACL is considerably weaker than the native ACL during the first 12 months, so a brace during this early period helps protect it from harmful forces that occur in everyday life or in sports activity.

SUMMARY

A brace configured for attachment to a joint of a subject is provided. The brace includes a first arm having a first end and a second end. The brace includes a second arm having a first end and a second end. The brace includes a hinge coupling the first end of the first arm with the first end of the second arm such that the first arm and the second arm are movable to different relative angular orientations. The brace includes a potentiometer coupled to the hinge.

A method of monitoring the relative angular orientation of a first arm of a brace relative to a second arm of the brace is provided. The method includes monitoring an output of a potentiometer coupled to one of the first arm and the second arm.

DETAILED DESCRIPTION

Figure 1:
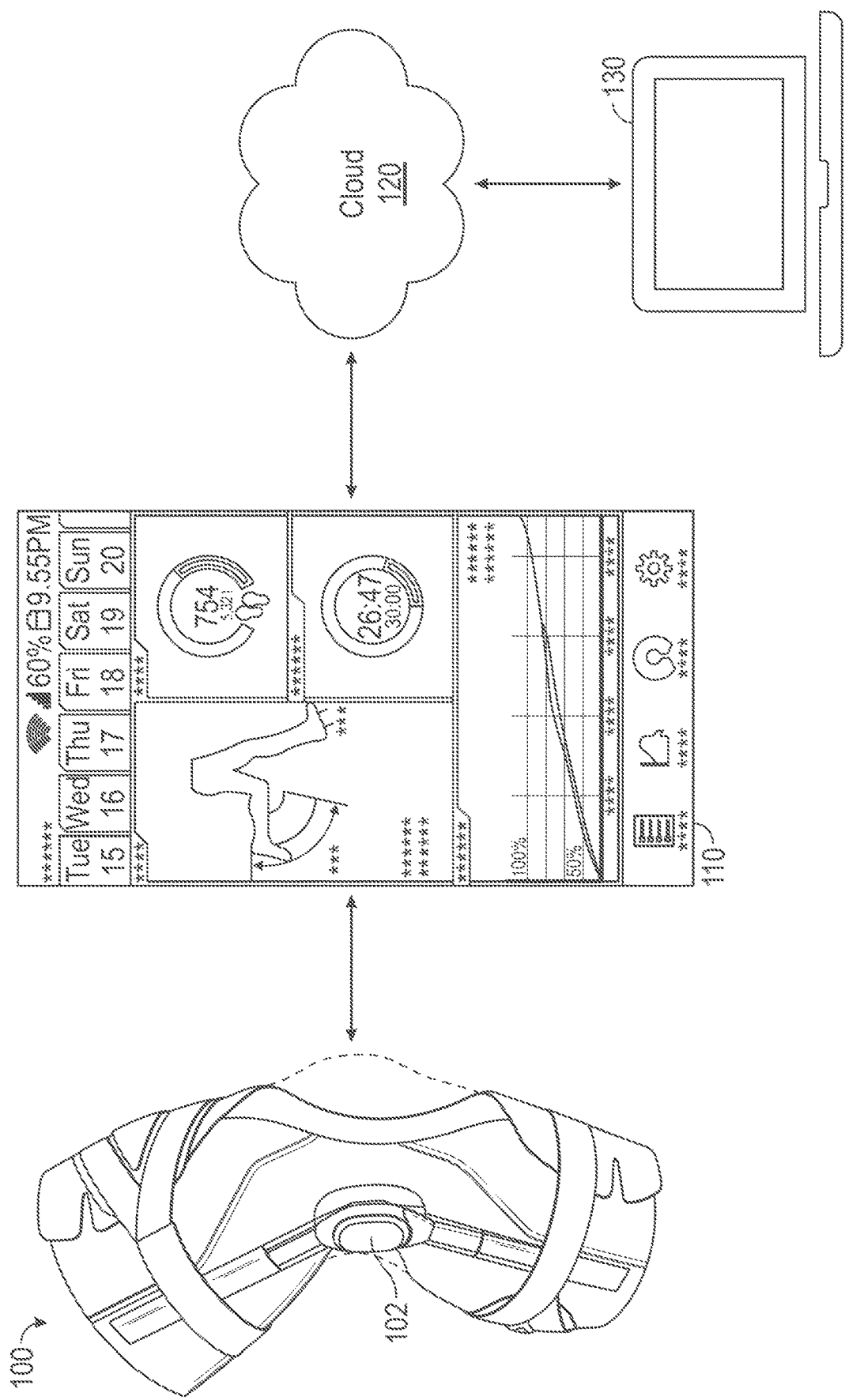
FIG. 1 illustrates a system comprising a brace having an integrated remote patient monitoring device, in accordance with some embodiments.

Embodiments of this disclosure relate to orthopedic braces for use in treating a variety of injuries to the knee, or other joint, and surrounding ligaments. More particularly, embodiments of the brace disclosed herein may be intended for use in activities of daily living for patients with ACL deficiencies, collateral ligament deficiencies, hyperextension injury, or for prophylactic use.

Orthotic bracing and support can promote healing and wellness through the benefit of natural motion through safe ranges of motion (ROM). However, efficacy of such bracing and support in promoting healing and wellness may be at least partially dependent upon whether the patient being apprised of whether they are using the brace as intended, whether recovery is progressing as expected, and/or whether predetermined goals are being reached as dictated by the treating physician. In addition, a physician's ability to guide post-surgical recovery of the patient may be at least partially dependent upon the physician's being apprised of whether the patient is using the brace as expected, recovery is progressing as expected, and/or how engaged the patient is in the recovery process. Accordingly, there is a need for solutions that provide such feedback to one or both of the patient and the treating physician.

The braces as described and/or claimed herein address shortcomings of prior art devices at least in part by providing doctors a way to more effectively manage and track patient post-surgical care and rehabilitation through an integrated patient activity monitor attached to or integrated in a post-surgical brace that intermittently or continuously captures, tracks and reports patient mobility, activity and protocol compliance, allowing such doctors to provide virtual therapy and advance warning for high risk patients needing additional post-surgery support.

The braces described and/or claimed herein further provide patients a way to track their progress against their post-surgical protocols and tools to better manage their physical therapy. As will be described in more detail below, in some embodiments, a mobile smart device, combined with a platform for virtual therapy, frequently asked questions (FAQs) and mobility support may allow such patients to better self-manage care and track rehabilitation progress before visits to the doctor, which may provide more flexibility to alert and communicate with their doctors about their post-surgical care effectively.

A better understanding of the various features of the disclosure can be gleaned from the following description read in conjunction with the accompanying drawings in which like reference characters refer to like elements, where reasonably applicable. While the disclosure may be susceptible to various modifications and alternative constructions, certain illustrative features are shown in the drawings and are described in detail below. It will be understood, however, that there is no intention to limit the disclosure to the specific embodiments disclosed, but to the contrary, the intention is to cover all modifications, alternative constructions, combinations, and equivalents falling within the spirit and scope of the disclosure.

Furthermore, it will be appreciated that unless a term is expressly defined in this disclosure to possess a described meaning, there is no intent to limit the meaning of such term, either expressly or indirectly, beyond its plain or ordinary meaning.

For ease of understanding the disclosed features of an orthopedic device, as used herein, "proximal" has its ordinary meaning and refers to a location situated next to or near the point of attachment or origin or a central point, or located toward the center of the body. Likewise, the term "distal" has its ordinary meaning and refers to a location that is situated away from the point of attachment or origin or central point, or located away from the center of the body. The term "medial" refers to a position that is closer to the midline of the body, whereas the term "lateral" refers to a position further from the midline of the body. The terms "upper" and "lower" describe the position of certain elements as being either above or below the hinge portions of the brace assembly. An "upper" element is above the hinge and knee or other joint, whereas a "lower" element is below the hinges and knee or other joint. The term "posterior" also has its ordinary meaning and refers to a location that is behind or to the rear of another location or feature. Lastly, the term "anterior" has its ordinary meaning and refers to a location that is ahead of or to the front of another location or feature.

The terms "rigid," "flexible," "malleable" and "resilient" may be used herein to distinguish portions of certain features of the orthopedic device. The term "rigid" is intended to mean an element of the device is generally or substantially inflexible. Within the context of frame or support members or shells that are "rigid," it is intended to indicate that they do not lose their overall shape when force is applied. The term "flexible" or "malleable", by contrast, is intended to encompass features that are capable of bending or flexing under load.

FIG. 1 illustrates a system comprising a brace 100 having an integrated remote patient monitoring device 102, in accordance with some embodiments. FIG. 1 further illustrates a user smart phone 110 or other suitable communication device, cloud-based database, portal and/or communication network 120, and user and/or physician communication device 130, each of which may be configured as described below.

Remote patient monitoring device 102 may comprise a goniometer (not shown in FIG. 1) configured to measure an angle, a rotation, a range of motion, an angular velocity and/or acceleration of a user's joint, or any average, peak, minimum or maximum value of any of these aspects. Device 102 may additionally utilize such measurements alone or in conjunction with measurements of other types of sensors, as described below, to determine a number of steps taken, a distance traveled, ground contact force, or a time period taken by the patient to stand up and begin ambulation, among other determinations.

In some embodiments, device 102 may further comprise one or more accelerometers configured to measure an acceleration of a portion of the user's limb, gyroscopes configured to measure an orientation of a portion of the user's limb and/or a chance in that orientation, contact and/or non-contact thermometers configured to measure a skin temperature and/or an ambient temperature, capacitive and/or magnetic proximity sensors, humidity and/or moisture sensors configured to measure an ambient humidity level or moisture level of a portion of brace 100, and/or light sensors configured to measure ambient light levels. In some embodiments, device 102 may be waterproof at least to the satisfaction of IPX7 standards.

Accordingly, device 102 may be configured to measure, determine or estimate parameters such as peak varus and/or valgus force during gait, rotation and/or pivot shift forces, average and/or peak range of motion and/or joint angle during flexion and/or extension alone or as a function of post-operative time, ACL shear, brace movement and/or slippage, ground reaction force, quadricep-to-hamstring strength ratios, acceleration and/or speed of the patient, a portion of a patient's limb, or brace 100, and/or any other characteristic desirable for post-operative physical therapy and or rehabilitation of a patient's joint.

Device 102 may be powered by one or more replaceable, non-replaceable, rechargeable, non-rechargeable batteries (not shown in FIG. 1), or any other suitable electrical power source. Accordingly, once enabled, device 102 may be configured to monitor and record continuous operation without substantive interaction from the patient for more than 30 days, for example, without battery recharge or replacement. In some embodiments, recharging of such a batter may be accomplished by standard AC or DC charging systems, or by built-in energy harvesting devices (also not shown in FIG. 1), such as solar, vibration, thermal, kinetic and/or magnetically inductive charging devices. Device 102 is configured to capture in real-time, store, and intermittently, periodically, or continuously transmit data related to such above-described indications of patient activity and physical therapy compliance to smart phone 110 or other suitable communication device.

Smart phone 110 or other suitable communication device may have one or more applications running thereon configured to receive and display the above-described data transmitted from device 102. In some embodiments, smart phone 110 may be configured, through such one or more applications, to continuously, periodically, or intermittently transmit the above-described data to cloud-based database, portal and/or communication network 120.

Smart phone 110 or other suitable communication device may be further configured, through such one or more applications, to provide patient account setup features, patient login features, the ability to connect and download the above-described patient activity and physical therapy compliance data from device 102 via wired or wireless connection. Smart phone 110 or other suitable communication device may be further configured, through such one or more applications, to allow the patient to view the activity and compliance data, to view and compare prescribed activity and compliance goals with actual activity and compliance indications, and/or to compare personal recovery rate with that of the general population under similar circumstances.

Smart phone 110 or other suitable communication device may be further configured, through such one or more applications, to download activity monitor firmware from cloud-based database, portal and/or communication network 120 or another source and transfer the firmware to device 102 through either wired or wireless communication. Smart phone 110 or other suitable communication device may be further configured, through such one or more applications, to download activity monitor operational parameters from cloud-based database, portal and/or communication network 120 and transfer such parameters to device 102.

Cloud-based database, portal and/or communication network 120 may be configured to store any data received from at least device 102, smart phone 110 or other suitable communication device, and/or device 130.

Device 130 may comprise a computer, mobile device, or any other suitable communication device and may be configured to run one or more applications that allow device 130 to access cloud-based database, portal and/or communication network 120 utilizing a standard web browser, for example Internet Explorer. Utilizing such one or more applications, device 130 may provide account setup features, patient account login features, and/or prescribing physician or other practitioner login features. Device 130 may provide the patient and/or the prescribing physician with the ability to receive, securely store, and format for remote viewing, such patient activity and compliance data, alerts as to patient progress concerning range of motion, step counting and/or activity level, send and receive messages to and from the patient, and even receive photos or videos of a wound from the patient. Upon remotely viewing such patient activity and compliance data, the prescribing physician may advantageously provide feedback to the patient regarding established physician-prescribed goals, encourage and track patient compliance with such goals, and/or update or alter such goals and protocols.

Accordingly, the system described in connection with FIG. 1 may allow a patient to receive feedback as to whether they are using the brace as intended, whether recovery is progressing as expected, and/or whether they are reaching their goals as dictated by their physician. In addition, physicians may receive feedback as to whether the patient is using brace 100 as expected, whether the patient is progressing as expected, and/or how engaged the patient is in the recovery process. Such advantages reduce a number of touch points between the patient and their health care provider, reduce the length of stay, readmissions and extra visits to the health care provider, reduce physical therapy costs, and improve patient satisfaction.

Several embodiments of braces corresponding to brace 100 of FIG. 1 will now be described in connection with at least FIGS. 2A-10.

Figure 2B:
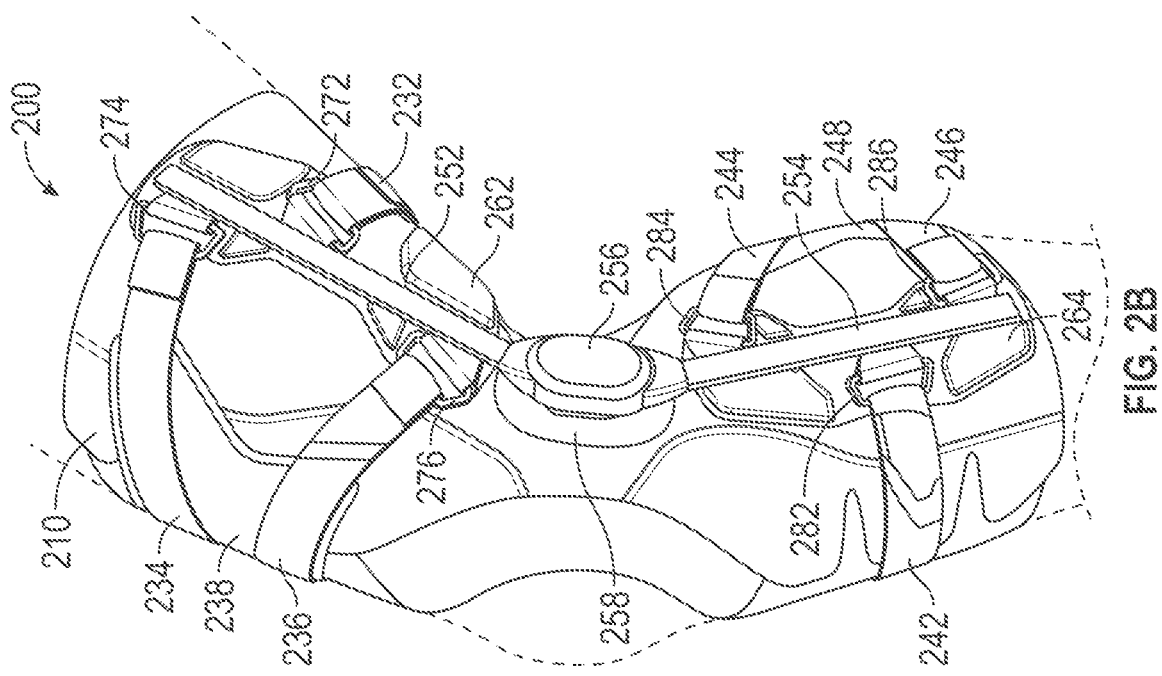
FIG. 2B illustrates a perspective view of a lateral side of the brace of FIG. 2A.
Figure 2A:
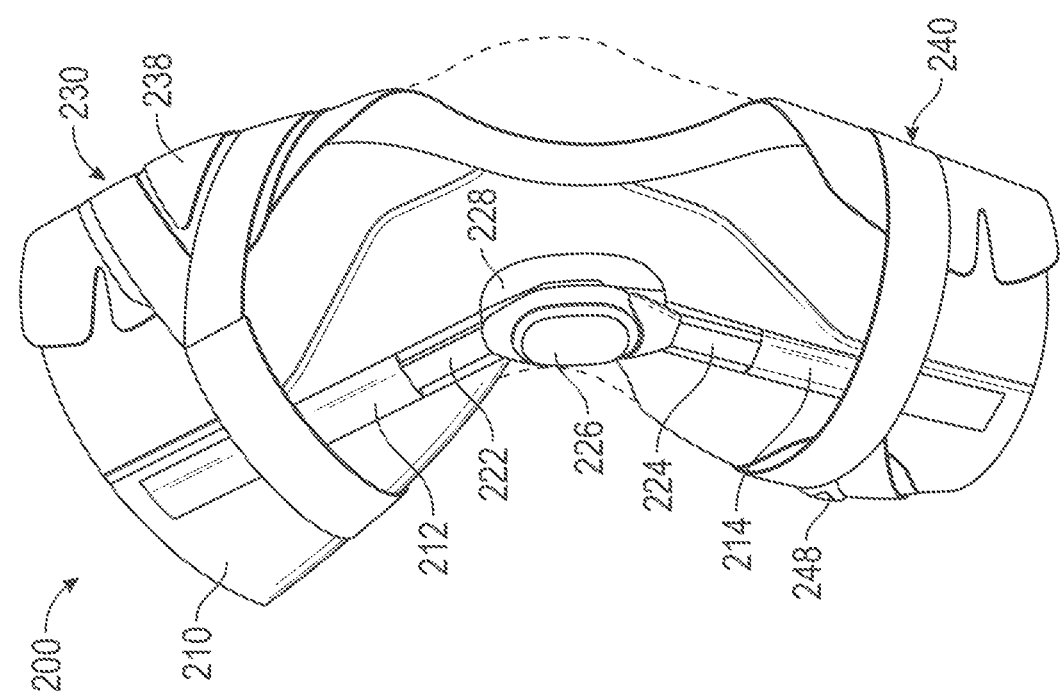
FIG. 2A illustrates a perspective view of a medial side of a brace, in accordance with some embodiments.

FIG. 2A illustrates a perspective view of a medial side of a brace 200, in accordance with some embodiments, while FIG. 2B illustrates a perspective view of a lateral side of brace 200, in accordance with some embodiments. FIGS. 2A and 2B will be described together below.

Brace 200 comprises a first medial arm 222 coupled to a second medial arm 224 via a medial hinge assembly 226. The terms "hinge" or "hinge assembly" as used herein means a mechanical coupler that ties two arms of the brace together while allowing rotational motion through different angular orientations of the longitudinal axes of the two arms. When in use, the hinge of a brace is generally proximate to the anatomical joint being braced. First medial arm 222 may be configured to be disposed along a medial side of an upper leg of the patient. Accordingly, in some embodiments, first medial arm 222 may be bent at an angle that allows first medial arm 222 to be so disposed when medial hinge assembly 226 is disposed on or adjacent to a medial side of the patient's knee. Second medial arm 224 may be configured to be disposed along a medial side of a lower leg of the patient. Accordingly, in some embodiments, second medial arm 224 may be bent at an angle that allows second medial arm 224 to be so disposed when medial hinge assembly 226 is disposed on or adjacent to the medial side of the patient's knee. In some embodiments, first and second medial arms 222, 224 may comprise metal, for example aluminum, or any other substantially rigid material. In some embodiments, each of first and second medial arms 222, 224 may be approximately 0.625 inches wide, approximately 0.100 inches thick, and approximately 5.25 inches long from hinge center to bar end. However, the present disclosure is not so limited and first and second medial arms 222, 224 may have any suitable dimensions, which may be the same or different from one another.

Brace 200 may further comprise a medial condyle pad 228 configured to be disposed between medial hinge assembly 226 and the medial side of the patient's knee. In some embodiments, medial condyle pad 228 may comprise foam, rubber, an elastomer, plastic, 2#EVA, Lycra laminate, brush nylon, or any other suitable material, thermoformed or otherwise, for providing a cushion between medial hinge assembly 226 and the medial side of the patient's knee. In some embodiments, medial condyle pad 228 may be secured to hinge assembly 226 via any suitable method, for example, hook and loop fasteners, snaps, clips, rivets, an adhesive, etc.

Brace 200 may further comprise a wrap 210 configured to be wrapped and secured around at least portions of the patient's upper leg, knee and lower leg. Wrap 210 comprises a first pocket 212 configured to receive and secure at least a portion of first medial arm 222 and a second pocket 214 configured to receive and secure at least a portion of second medial arm 224. Wrap 210 may comprise breathable foam, Lycra, nylon, or any other suitable material.

Brace 200 further comprises a first lateral arm 252 coupled to a second lateral arm 254 via a lateral hinge assembly 256. First lateral arm 252 may be configured to be disposed along a lateral side of an upper leg of the patient. Accordingly, in some embodiments, first lateral arm 252 may be bent at an angle that allows first lateral arm 252 to be so disposed when lateral hinge assembly 256 is disposed on a lateral side of the patient's knee. Second lateral arm 254 may be configured to be disposed along a lateral side of a lower leg of the patient. Accordingly, in some embodiments, second lateral arm 254 may be bent at an angle that allows second lateral arm 254 to be so disposed when lateral hinge assembly 256 is disposed on or adjacent to the lateral side of the patient's knee. In some embodiments, first and second lateral arms 252, 254 may comprise metal, for example aluminum, or any other substantially rigid material. In some embodiments, each of first and second lateral arms 252, 254 may be approximately 0.625 inches wide, approximately 0.100 inches thick, and approximately 5.25 inches long from hinge center to bar end. However, the present disclosure is not so limited and first and second lateral arms 252, 254 may have any suitable dimensions, which may be the same as or different from one another. As described in connection with FIGS. 3A and 5A-6 below and previous FIG. 1 above, lateral hinge assembly 256 may include integrated remote patient monitoring device 102 configured to measure one or more of an angle, a rotation, a range of motion, an angular velocity and/or acceleration of a user's joint.

The integrated remote patient monitoring device is configured to: receive signals from the potentiometer indicative of the different relative angular orientations of the first arm with respect to the second arm, determine at least one of a range of motion, an angular velocity and an acceleration of the joint of the patient based at least in part on the signals from the potentiometer when the brace is worn by the patient, and wirelessly transmit at least one of an indication of the signals from the potentiometer and an indication of the determination to a communication device.

Brace 200 may further comprise a lateral condyle pad 258 configured to be disposed between lateral hinge assembly 256 and the lateral side of the patient's knee. In some embodiments, lateral condyle pad 258 may comprise foam, rubber, an elastomer, plastic, 2#EVA, Lycra laminate, brush nylon, or any other suitable material, thermoformed or otherwise, for providing a cushion between lateral hinge assembly 256 and the lateral side of the patient's knee. In some embodiments, lateral condyle pad 258 may be secured to hinge assembly 256 via any suitable method, for example, hook and loop fasteners, snaps, clips, rivets, an adhesive, etc.

Brace 200 may further comprise an upper pad 262 configured to be disposed between first lateral arm 252 and a lateral side of the patient's upper leg. Upper pad 262 may comprise foam, rubber, an elastomer, plastic, 2#EVA, Lycra laminate, brush nylon, or any other suitable material, thermoformed or otherwise, for providing a cushion between first lateral arm 252 and the lateral side of the patient's upper leg. In some embodiments, upper pad 262 may be secured to first lateral arm 252 via any suitable method, for example, hook and loop fasteners, snaps, clips, rivets, an adhesive, etc.

Brace 200 may further comprise a lower pad 264 configured to be disposed between second lateral arm 254 and a lateral side of the patient's lower leg. Lower pad 264 may comprise foam, rubber, an elastomer, plastic, 2#EVA, Lycra laminate, brush nylon, or any other suitable material, thermoformed or otherwise, for providing a cushion between second lateral arm 254 and the lateral side of the patient's lower leg. In some embodiments, lower pad 264 may be secured to second lateral arm 254 via any suitable method, for example, hook and loop fasteners, snaps, clips, rivets, an adhesive, etc.

Brace 200 may further comprise an upper strap 230 configured to secure one or more of upper pad 262, first lateral arm 252 and upper medial arm 222 to the upper leg of the patient. In some embodiments, upper strap 230 may comprise a "Y"-shaped strap comprising a first end 232 branching off at a junction to form each of a second end 234 and a third end 236. Each of first, second and third ends 232, 234, 236 may be secured to at least one of upper pad 262 and first lateral arm 252 via respective fastening elements 272, 274, 276. In some embodiments, fastening elements 272, 274, 276 may comprise D-rings. However, the present disclosure is not so limited and upper strap 230 may comprise any suitable type of restraining element secured to one or more of upper pad 262 and first lateral arm 252 by any suitable method. As shown in FIGS. 2A and 2B, upper strap 230 may wrap around the upper leg of the patient such that first end 232 is disposed around a posterior portion of the patient's upper leg, while second and third ends 234, 236 are disposed around an anterior portion of the patient's upper leg. However, the present disclosure is not so limited and upper strap 230 may be configured in the reverse orientation of that shown in FIGS. 2A and 2B. In some embodiments, upper strap 230 may be trimmable to an appropriate length for the patient.

In some embodiments, brace 200 may further comprise a thigh pad 238 configured to be disposed between and secured in place by upper strap 230 and the thigh of the patient. Thigh pad 238 may comprise foam, rubber, an elastomer, plastic, 2#EVA, Lycra laminate, brush nylon, or any other suitable material, thermoformed or otherwise, for providing a cushion between upper strap 230 and the thigh of the patient.

Brace 200 may further comprise a lower strap 240 configured to secure one or more of lower pad 264, second lateral arm 254 and lower medial arm 224 to the lower leg of the patient. In some embodiments, lower strap 240 may comprise a "Y"-shaped strap comprising a first end 242 branching off at a junction to form each of a second end 244 and a third end 246. Each of first, second and third ends 242, 244, 246 may be secured to at least one of lower pad 262 and first lateral arm 252 via respective fastening elements 282, 284, 286. In some embodiments, fastening elements 282, 284, 286 may comprise D-rings. However, the present disclosure is not so limited and lower strap 240 may comprise any suitable type of restraining element secured to one or more of lower pad 262 and first lateral arm 252 by any suitable method. As shown in FIGS. 2A and 2B, lower strap 240 may wrap around the lower leg of the patient such that first end 242 is disposed around an anterior portion of the patient's lower leg, while second and third ends 244, 246 are disposed around a posterior portion of the patient's lower leg. However, the present disclosure is not so limited and lower strap 240 may be configured in the reverse orientation of that shown in FIGS. 2A and 2B. In some embodiments, lower strap 240 may be trimmable to an appropriate length for the patient.

In some embodiments, brace 200 may further comprise a calf pad 248 configured to be disposed between and secured in place by lower strap 240 and the calf of the patient. Calf pad 248 may comprise foam, rubber, an elastomer, plastic, 2#EVA, Lycra laminate, brush nylon, or any other suitable material, thermoformed or otherwise, for providing a cushion between lower strap 240 and the calf of the patient.

One example implementation of a lateral hinge assembly 256 will now be described in more detail in connection with FIG. 3A below. Although the first lateral arm 252, second lateral arm 254 and lateral hinge assembly 256 are described in connection with FIG. 3, first medial arm 232, second medial arm 234 and medial hinge assembly 236 may also or alternatively comprise substantially similar or the same features. Moreover, although certain functionality is described with respect to first lateral arm 252, such functionality may alternatively be applied to second lateral arm 254 or second medial arm 224.

Figure 3A:
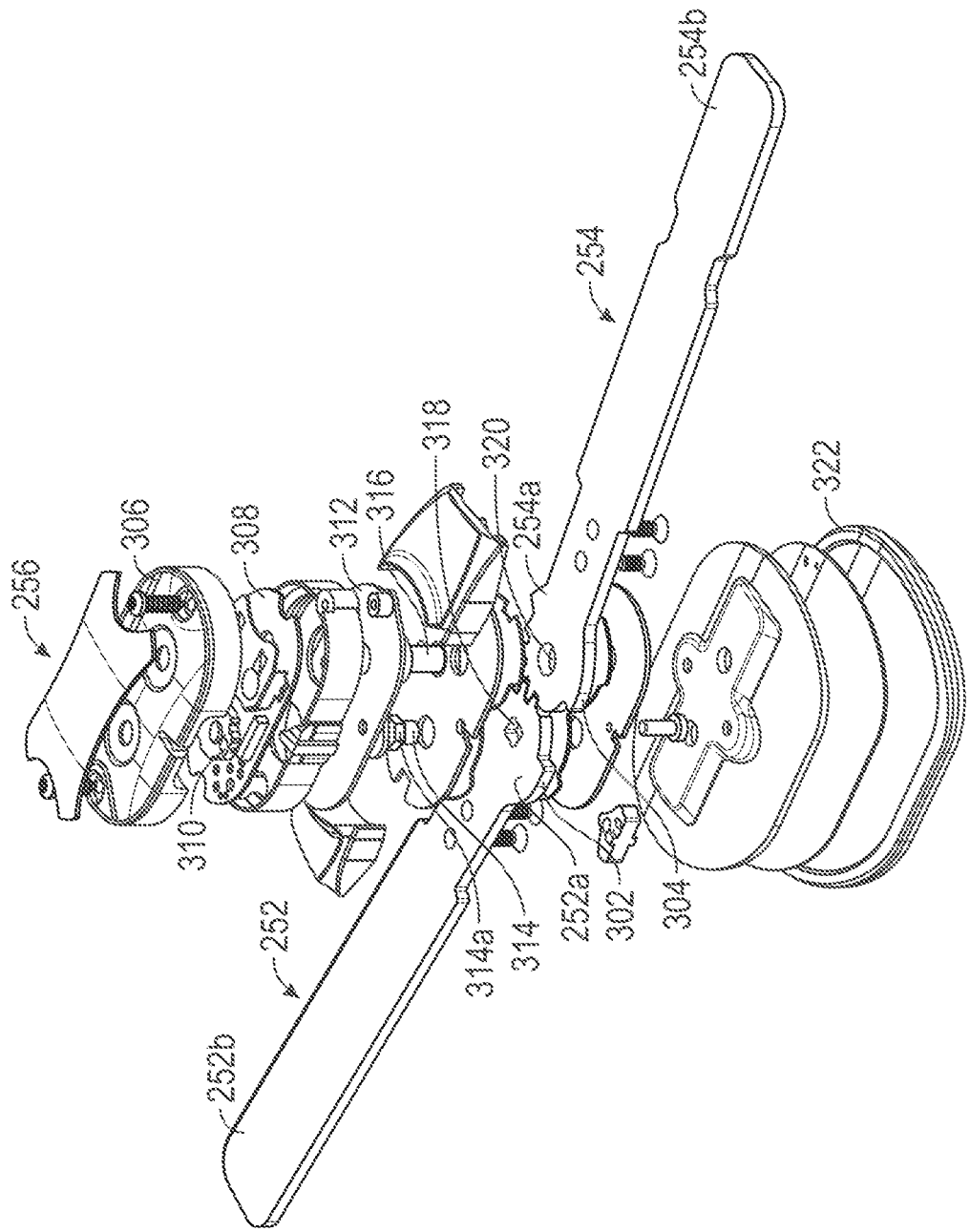
FIG. 3A illustrates an exploded perspective view of a hinge assembly of the brace of FIGS. 2A and 2B, in accordance with some embodiments.

FIG. 3A illustrates an exploded perspective view of lateral hinge assembly 256 of brace 200 of FIG. 2B, in accordance with some embodiments. Lateral hinge assembly 256 comprises an upper shell 306 configured to cover an outer-facing surface of lateral hinge assembly 256. Lateral hinge assembly 256 further comprises at least one printed circuit board (PCB) 308 comprising a rotation/angle encoder mounted to PCB 308 configured to measure and/or track one or more aspects of joint function as described anywhere in this disclosure. As will be described in more detail in connection with FIGS. 3B-3C and 5A-6, in some embodiments, rotation/angle encoder 310 may be an analog mechanical potentiometer, a digital potentiometer, or any other type of electrical potentiometer or rotational encoder configured to present a resistance that varies based on a position of a rotatable shaft of rotation/angle encoder 310. In some embodiments, PCB 308, comprising rotation/angle encoder 310, may form at least a portion of remote patient monitoring device 102 as previously described in connection with FIG. 1. Accordingly, in some embodiments, PCB 308 may further comprise one or more of the sensors and/or elements as previously described in connection with FIG. 1 as well as any additional circuitry required for any functionality described in this specification.

As shown in FIG. 3A, first lateral arm 252 comprises a first end 252a and a second end 252b, and second lateral arm 254 comprises a first end 254a and a second end 254b. Lateral hinge assembly 256 may further comprise a hinge plate 312 configured to couple first end 252a of first lateral arm 252 with first end 254a of second lateral arm 254, via first shaft 314 and second shaft 316, respectively, such that first lateral arm 252 and second lateral arm 254 are movable to different relative angular orientations, in some embodiments, with respect to hinge assembly 256. In some embodiments, first shaft 314 may correspond to or alternatively be coupled to the rotatable shaft of the rotation/angle encoder 310. A portion 314a of rotatable shaft 314 of rotation/angle encoder 310 may be keyed or otherwise shaped to rotationally engage a mating aperture 318 in first end 252a of first lateral arm 252, thereby coupling rotatable shaft 314 to first end 252a of first lateral arm 252. Accordingly, rotatable shaft 314 may have a fixed angular orientation with respect to first end 252a of first lateral arm 252. Further, second shaft 316 may be configured to fit within a second aperture 320 in first end 254a of second lateral arm 254.

In some embodiments, first end 252a of first lateral arm 252 may comprise at least one stop 302 configured to limit extension and/or flexion of the patient's joint about lateral hinge assembly 256. Similarly, in some embodiments, first end 254a of second lateral arm 254 may comprise at least one stop 304 configured to limit extension and/or flexion of the patient's joint about lateral hinge assembly 256. In some embodiments, one or both of first ends 252a, 254a may comprise an additional stop (not shown) located substantially opposite respective stops 302, 304 configured to limit extension and/or flexion of the patient's joint in an opposite direction.

Lateral hinge assembly 256 may further comprise a back cover 322. In some embodiments, lateral hinge assembly 256 may further comprise a light, for example a blue light emitting diode (LED) (not shown), configured to indicate whether electronics of PCB 308 are currently powered ON or OFF.

In one advantageous embodiment, the rotation/angle encoder comprises a potentiometer. Examples of potentiometers will now be described in connection with FIGS. 3B and 3C. For the purposes of this disclosure, a potentiometer is an electrical component or set of interconnected components that function as a variable 3-terminal resistor and/or that provide voltage divider functionality between those 3 terminals.

Figure 3B:
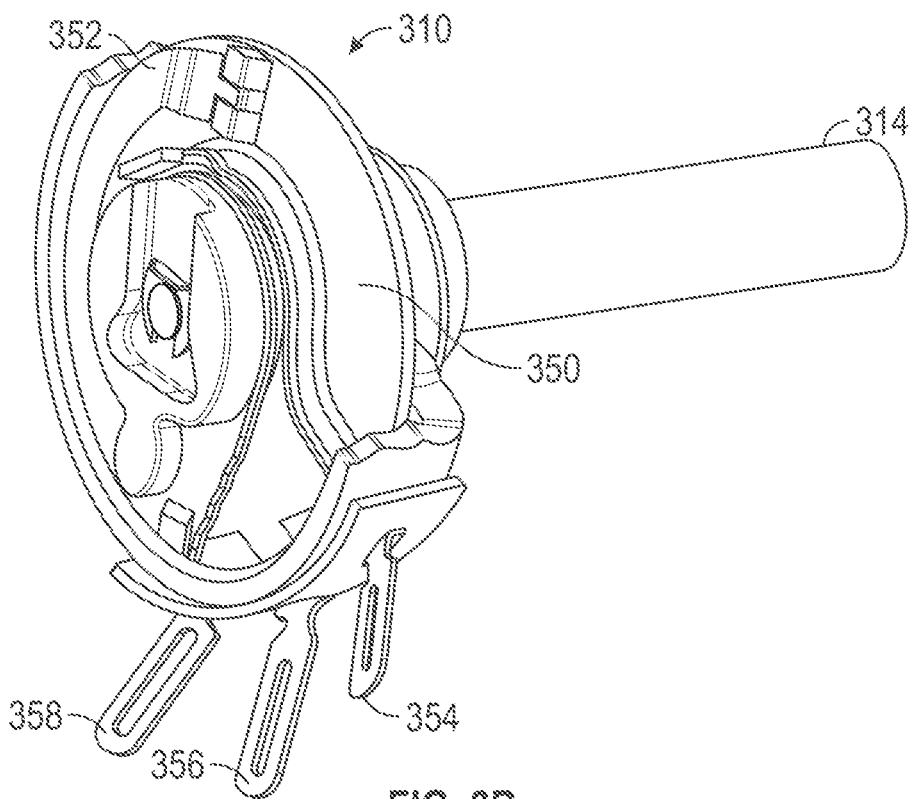
FIG. 3B illustrates an example analog potentiometer, in accordance with some embodiments.

FIG. 3B illustrates rotation/angle encoder 310 as an analog potentiometer, in accordance with some embodiments. Examples of analog potentiometers include but are not limited to slider pots, thumbwheel pots, and trimmer pots. As illustrated in FIG. 3B, potentiometer 310 comprises a first terminal 354 coupled to a first end of a resistive element 350, a second terminal 358 coupled to a second end of resistive element 350, and a third terminal 356 coupled to a sliding contact 352. Sliding contact 352 is coupled to rotatable shaft 314 and is configured to make contact with resistive element 350 at a position that depends on an angular orientation of rotatable shaft 314. In some embodiments, resistive element 350 may have a substantially semicircular shape such that sliding contact 352 can make contact with at any point along resistive element 350 while rotating about an axis defined by an axial center of rotatable shaft 314. In some other embodiments, resistive element 350 may be substantially linear in shape and sliding contact 352 may make contact with any point along resistive element 350 while rotating about the axis defined by the axial center of rotatable shaft 314. In some embodiments, resistive element 350 may comprise any one or more of graphite, resistance wire, carbon particles suspended in plastic, a ceramic/metal mixture, a resistive polymer or resin paste, or any other suitable relatively high-resistance conductive material. In some embodiments, a resistance provided by resistive element 350 between first terminal 354 and third terminal 356 may increase linearly with angular orientation of rotatable shaft 314. In some other embodiments, the resistance provided by resistive element 350 between first terminal 354 and third terminal 356 may increase in a non-linear fashion with angular orientation of rotatable shaft 314, for example, exponentially, logarithmically, or in any other non-linear fashion.

As will be described in more detail in connection with FIG. 6, in operation, a first voltage is provided across first and second terminals 354, 358. Based on an angular orientation of rotatable shaft 314, sliding contact 352 makes contact with a single, variable position on resistive element 350. Accordingly, the portion of resistive element 350 in an electrical path between first terminal 354 and third terminal 356 provides a first variable resistance, and the portion of resistive element 350 in an electrical path between third terminal 356 and second terminal 358 provides a second variable resistance, where a sum of the first and second variable resistances is generally equal to the total resistance of resistive element 350. A second voltage appearing between third terminal 356 and the second terminal 358 is related to and/or proportional to a ratio between the second variable resistance and the total resistance of resistive element 350. Alternatively, a third voltage appearing across the first terminal 354 and third terminal 356 is related to and/or proportional to a ratio between the first variable resistance and the total resistance of resistive element 350. Accordingly, potentiometer 310 functions as a voltage divider where either the second voltage or the third voltage may vary with, and be utilized as an indicator of, an angular orientation of rotatable shaft 314. Since first lateral arm 252 of FIGS. 2A-3A is attached to rotatable shaft 314, the second voltage or the third voltage may vary with and be utilized as an indicator of an angular orientation of first lateral arm 252 and of the patient's joint when secured in brace 200.

Figure 3C:
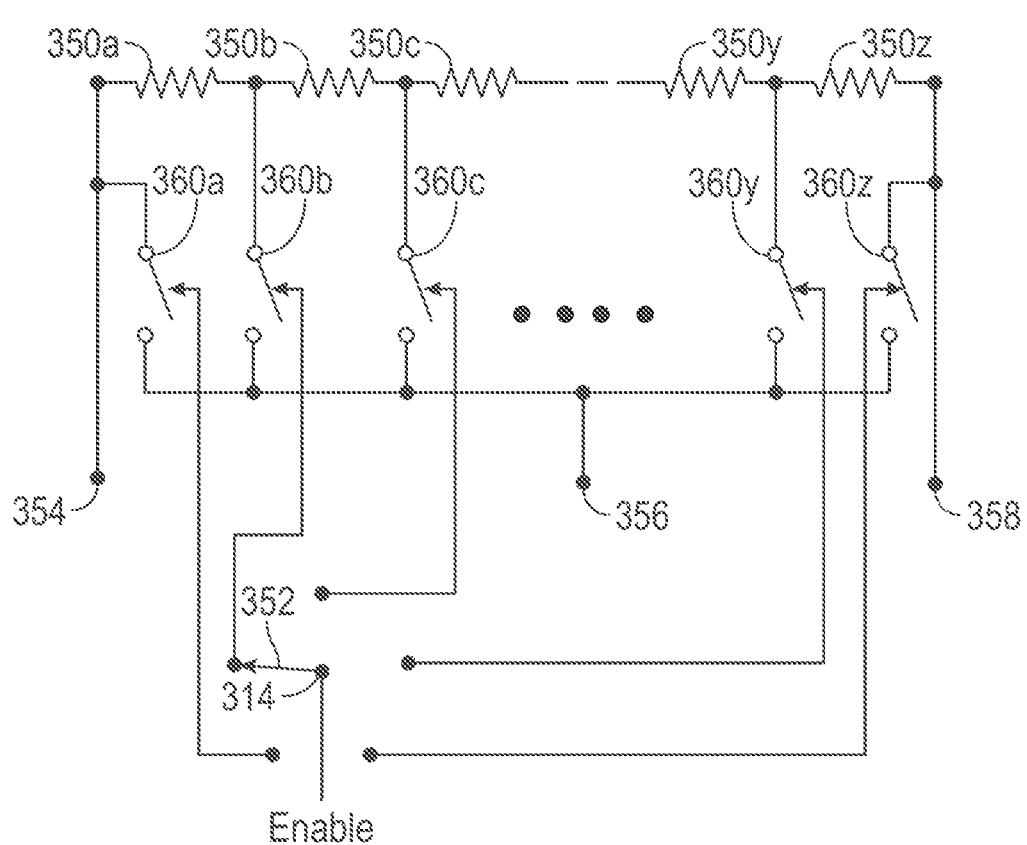
FIG. 3C illustrates an example digital potentiometer, in accordance with some embodiments.

FIG. 3C illustrates potentiometer 310 as a digital potentiometer, in accordance with some embodiments. As illustrated in FIG. 3C, potentiometer 310 comprises first terminal 354 coupled to a first end of a resistive element comprising a plurality of series-connected resistors 350a, 350b, 350c . . . 350y, 350z (also referred to herein as a resistor ladder), a second terminal 358 coupled to a second end of the resistive element, and a third terminal 356. Connection points between terminals of adjacent resistors 350a-350z and between the resistor ladder and first and second terminals 254, 258 comprise unique nodes of the resistor ladder. Each of a plurality of switches 360a, 360b, 360c . . . 360y are connected between a respective node of resistor ladder and third terminal 356. Switches 360a-360z may be relays, transistors or any other form of electrically controllable switch. Sliding contact 352 is coupled to rotatable shaft 314 and is configured to make electrical contact with a control terminal of one of switches 360a-360z, the specific control terminal depending on an angular orientation of rotatable shaft 314. In some embodiments, a resistance of each of resistors 350a-350z may be substantially the same such that a resistance provided between first terminal 354 and third terminal 356 may increase linearly, in a stepwise fashion, with angular orientation of rotatable shaft 314. In some other embodiments, the resistance of each of resistors 350a-350z may not be substantially the same such that the resistance provided between first terminal 354 and third terminal 356 may increase in a non-linear, stepwise fashion with angular orientation of rotatable shaft 314, for example, exponentially, logarithmically, or in any other non-linear fashion. A number of steps in the resistor ladder is related to a number of resistors in the ladder. The present disclosure contemplates any number of steps in the resistor ladder.

As will be described in more detail in connection with FIG. 6, in operation, a first voltage is provided across first and second terminals 354, 358. Based on an angular orientation of rotatable shaft 314, sliding contact 352, which may be coupled to a voltage or signal suitable as an enabling signal, makes electrical contact with a control terminal of one of switches 360a-360z, closing that switch and providing an electrical path having a first variable resistance between first terminal 354 and third terminal 356 and an electrical path having a second variable resistance between third terminal 356 and second terminal 354. A sum of the first and second variable resistances is generally equal to the total resistance of the entire resistor ladder. A second voltage appearing between third terminal 356 and second terminal 358 is related to and/or proportional to a ratio between the second variable resistance and the total resistance of the resistor ladder. Alternatively, a third voltage appearing across first terminal 354 and third terminal 356 is related to and/or proportional to a ratio between the first variable resistance and the total resistance of the resistor ladder. Accordingly, potentiometer 310 functions as a voltage divider where either the second voltage or the third voltage may vary with, and be utilized as an indicator of, an angular orientation of rotatable shaft 314. Since first lateral arm 252 of FIGS. 2A-3A is attached to rotatable shaft 314, the second voltage or the third voltage may vary with and be utilized as an indicator of an angular orientation of first lateral arm 252 and of the patient's joint in brace 200.

Figure 4:
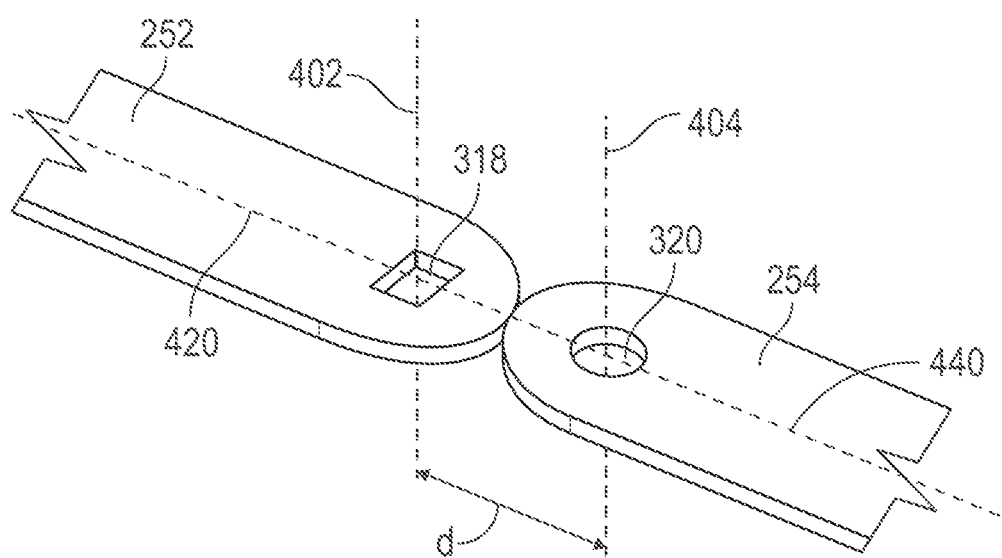
FIG. 4 illustrates a perspective view of respective first and second axes of rotation of the first and second arms of the brace of FIGS. 2A and 2B, in accordance with some embodiments.

As illustrated in FIG. 4, a first axis 402 of rotation of first lateral arm 252 passes substantially through the center of mating aperture 318, while a second axis 404 of rotation of second lateral arm 254 passes substantially through the center of aperture 320. First axis 402 is illustrated as being in parallel with and spatially, e.g., laterally, separated from second axis 404 by a fixed distance "d". As further illustrated in FIG. 4, lateral arm 252 defines a longitudinal axis 420 and lateral arm 254 defines a longitudinal axis 440. Relative to the printed circuit board 308 inside the hinge as described above, as the relative angular orientation of the two longitudinal axes 420, 440 changes, the orientation of the printed circuit board 308 will change by the same amount with reference to the openings 318 and 320. If the shaft 314 of a potentiometer 310 is rotationally fixed in opening 318, such as by having flats of other mating features on one or more sides, while the body of the potentiometer is fixed to the printed circuit board 308, then adjusting the orientation of the arms 252 and 254 will adjust the rotational position of the potentiometer shaft, changing the detected resistance thereof.

Figure 5A:
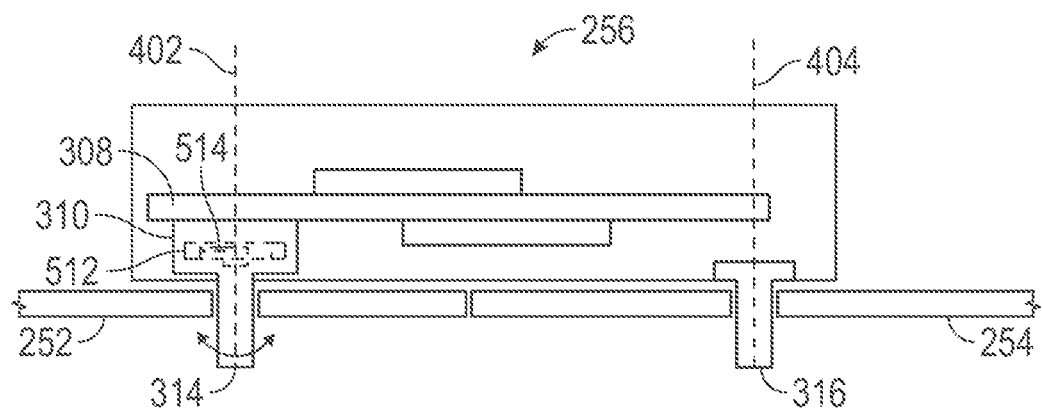
FIG. 5A illustrates a cutaway view of a portion of the brace of FIGS. 2A and 2B, in accordance with some embodiments.

FIG. 5A illustrates a cutaway view of a portion of the brace of FIGS. 2A and 2B, in accordance with some embodiments. Several portions of lateral hinge assembly 256 are shown, including PCB 308, potentiometer 310, first lateral arm 252 and second lateral arm 254. Rotatable shaft 314 of potentiometer 310 is illustrated as restraining first lateral arm 252 to rotate about first axis 402, while second shaft 316 is illustrated as restraining second lateral arm 254 to rotate about second axis 404. Potentiometer 310 is illustrated as previously described in connection with FIG. 3B, comprising, among other features, at least resistive element 350 and sliding contact 352. However digital embodiments, for example as previously described in connection with FIG. 3C, are also contemplated. Sliding contact 352 is coupled to rotatable shaft 314 and configured to make electrical contact with resistive element 350 at a position dependent upon the angular rotation of rotatable shaft 314 and sliding contact 352, while resistive element 350 may have a fixed orientation with respect to potentiometer 310 and lateral hinge assembly 256. As previously described, rotatable shaft 314 may be coupled to first lateral arm 252 such that, as first lateral arm 252 rotates about axis 402 (in and out of FIG. 5A), rotatable shaft 314 and sliding contact 352 will also rotate about axis 402, as indicated by the double-sided arrow. Accordingly, sliding contact 352 will contact resistive element 350 at varying positions, causing potentiometer to provide a correspondingly varying resistance. Thus, an output of potentiometer indicates a relative angular orientation of first lateral arm 252 with respect to second lateral arm 254. Moreover, since resistive element 350 has a fixed orientation with respect to potentiometer 310 and lateral hinge assembly 256, as first lateral arm 252 rotates rotatable shaft 314 and sliding contact 352, resistive element 350 is configured to rotate (or at least change orientation) with respect to first end 252a of first lateral arm 252.

Figure 5B:
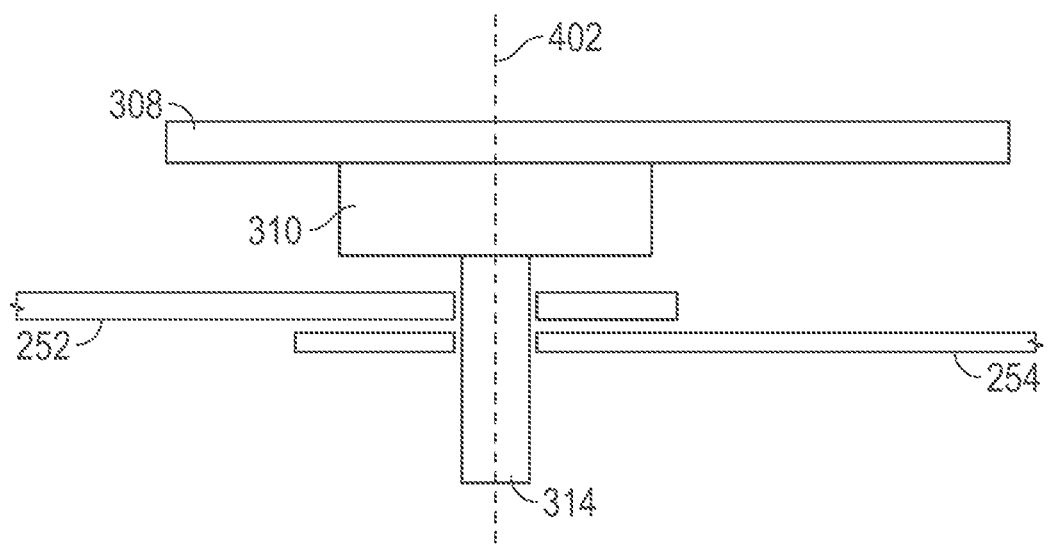
FIG. 5B illustrates a cutaway view of a portion of a brace, in accordance with some embodiments.

In some other embodiments, rather than first lateral arm 252 rotating about first axis 402 and second lateral arm 254 rotating about second axis 404, FIG. 5B illustrates an alternative embodiment where first lateral arm 252 and second lateral arm 254 are both configured to rotate about the same first axis 402. Accordingly, first lateral arm 252 may be secured to rotatable shaft 314 as previously described, while second lateral arm 254 is not secured to rotatable shaft 314 but is, instead, merely restrained to freely rotate about first axis 402 by rotatable shaft 314 while the orientation of the printed circuit board is fixed to lateral arm 254 by e.g. a stand-off 520. In such embodiments, all other functionality may be as previously described.

Figure 6:
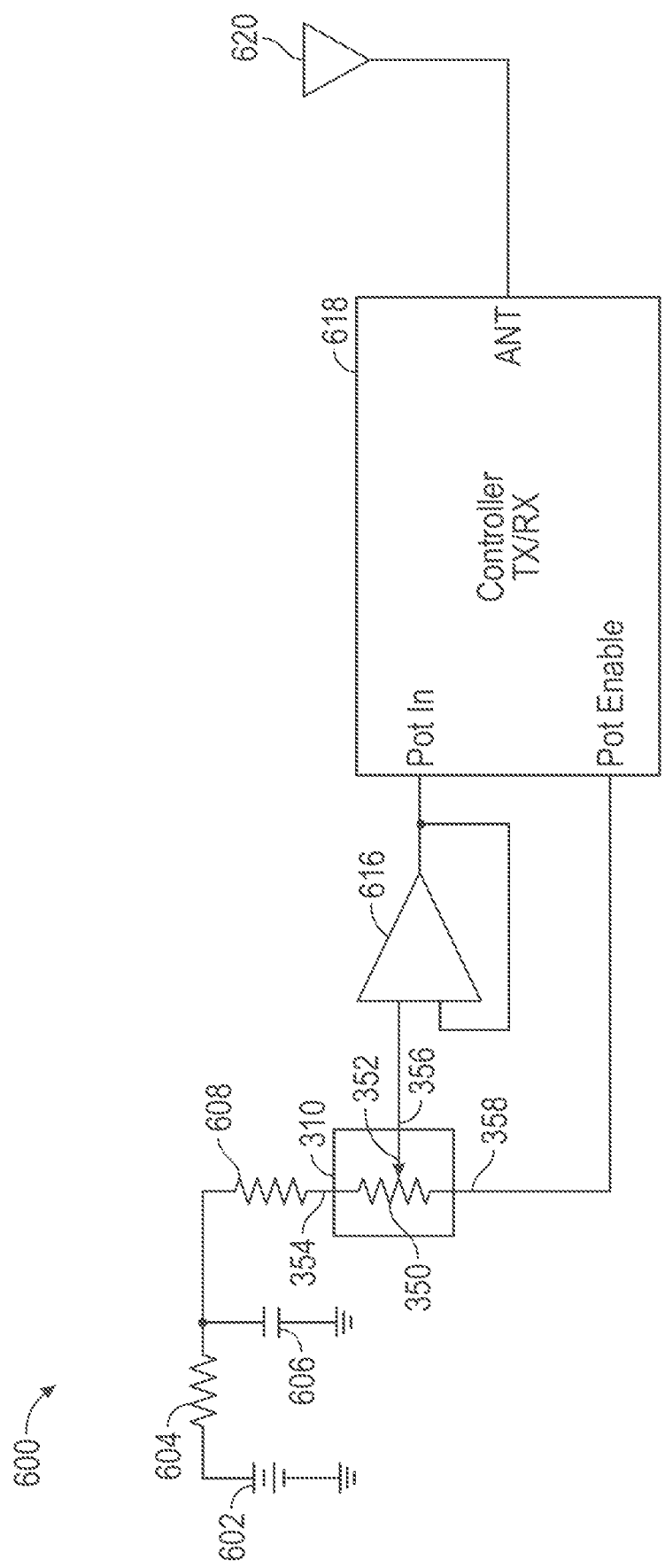
FIG. 6 illustrates a schematic diagram of an electrical circuit of a brace configured to monitor at least one aspect of patient joint motion, in accordance with some embodiments.

FIG. 6 illustrates a schematic diagram of an example electrical circuit 600 of a brace configured to monitor at least one aspect of patient joint motion, in accordance with some embodiments. Although one embodiment is disclosed in FIG. 6, the present disclosure is not so limited and contemplates any circuit or arrangement providing functionality as described in this disclosure.

PCB 308, as previously described, may comprise circuit 600. Circuit 600 may comprise a battery 602, a smoothing capacitor 606, first and second resistors 604, 608, potentiometer 310 having first, second and third terminals 354, 358, 356, resistive element 350 and sliding contact 352, a buffer 616, a controller 618 having transmitting and receiving capabilities, and an antenna 620. Although potentiometer 310 is illustrated as previously described in connection with FIG. 3B (e.g., an analog potentiometer), potentiometer 310 may also be as previously described in connection with FIG. 3C (e.g., a digital potentiometer).

Battery 606 has a negative terminal electrically connected to a ground potential and a positive terminal electrically connected to a first terminal of first resistor 604. Smoothing capacitor 606 has a first terminal electrically connected to the ground potential and a second terminal electrically connected to a second terminal of first resistor 604 and to a first terminal of second resistor 608. Second resistor 608 has a second terminal electrically connected to first terminal 354 of potentiometer 310 (e.g., a first terminal of resistive element 350), which may be considered an input of potentiometer 310. Second terminal 358 of potentiometer 310 (e.g., a second terminal of resistive element 350) is electrically connected to a potentiometer enable output of controller 618. Sliding contact 352 of potentiometer 310 is in electrical contact with a physical location on resistive element 350 that depends on an orientation of a rotatable shaft coupled to sliding contact 352, and with third terminal 356 of potentiometer 310. Third terminal 356 is in electrical contact with a first input terminal of buffer 616. An output terminal of buffer 616 is electrically connected to both a second input terminal of buffer 616 and a potentiometer input of controller 618. An antenna terminal of controller 618 is in electrical contact with antenna 620. Thus, an input of potentiometer 310 (e.g., first terminal 354) is electrically coupled to battery 602 through first and second resistors 604, 608. Although not shown, buffer 616 and controller 618 may each also be coupled to and receive power from battery 602 and may additionally be suitably coupled to the ground potential to complete an electrical circuit.

In operation battery 602, smoothing capacitor 606 and first and second resistors 604, 608 provide a predetermined voltage across first and second terminals 354, 358 of potentiometer 310 (e.g., across resistive element 350) when the potentiometer enable input of controller 618 is activated (e.g., electrically coupled to the ground potential or any other potential within circuit 600). Because sliding contact 352 makes electrical contact with varying physical positions on resistive element 350 depending on an angular orientation of a rotatable shaft of potentiometer 310 that is based on a degree of flexion or extension of the joint of the patient, potentiometer 310 operates as a voltage divider that outputs a variable proportion of the predetermined voltage to sliding contact 352, third terminal 356 and into buffer 616. Accordingly, the variable resistance provided between the input and output terminals of potentiometer 310, as well as the variable voltage provided at sliding contact 352, are proportional to and indicative of a relative angular orientation between first lateral arm 252 and second lateral arm 254, as previously described.

Buffer 616 provides a high impedance at its input with the output being equal to the voltage at sliding contact 352 to the potentiometer input of controller 618. A combination of high resistance values of resistive element 350 and the relatively high input impedance of buffer 616 also allow circuit 600 to draw extremely low amounts of current, and thus power, from battery 602, allowing uninterrupted operation of circuit 600 for relatively long periods of time (e.g., 6 months or more) without replacing or recharging battery 602. This is an especially advantageous feature in the environment of post-surgical recovery. Typically, such a brace is worn for a few months following surgery. With a low power potentiometer based rotation sensing circuit, continuous or near continuous rotation monitoring can be performed without a user needing to recharge or replace batteries in the hinge. As far as the user is concerned, the hinges on the brace are treated exactly like conventional hinges with no measurement capability, no maintenance whatsoever for the duration of the recovery period.

Controller 618 may be configured to convert the voltage received from the output of buffer 616 into a signal indicative of the received voltage and drive antenna 620 to transmit that signal to, for example, user smart phone 110 or other suitable communication device, as previously described in connection with FIG. 1. Accordingly, controller 618, alone or in conjunction with antenna 620, may comprise a wireless transmitter configured to transmit an indication of a relative angular orientation between first lateral arm 252 and second lateral arm 254 of brace 200, as a function of time and based on the received voltage, to user smart phone 110 or other suitable communication device, as previously described. In some embodiments, controller 618 may be further configured to receive and appropriately process a signal from antenna 620 that was transmitted from, for example, user smart phone 110 or other suitable communication device, as previously described in connection with at least FIG. 1.

Figure 7B:
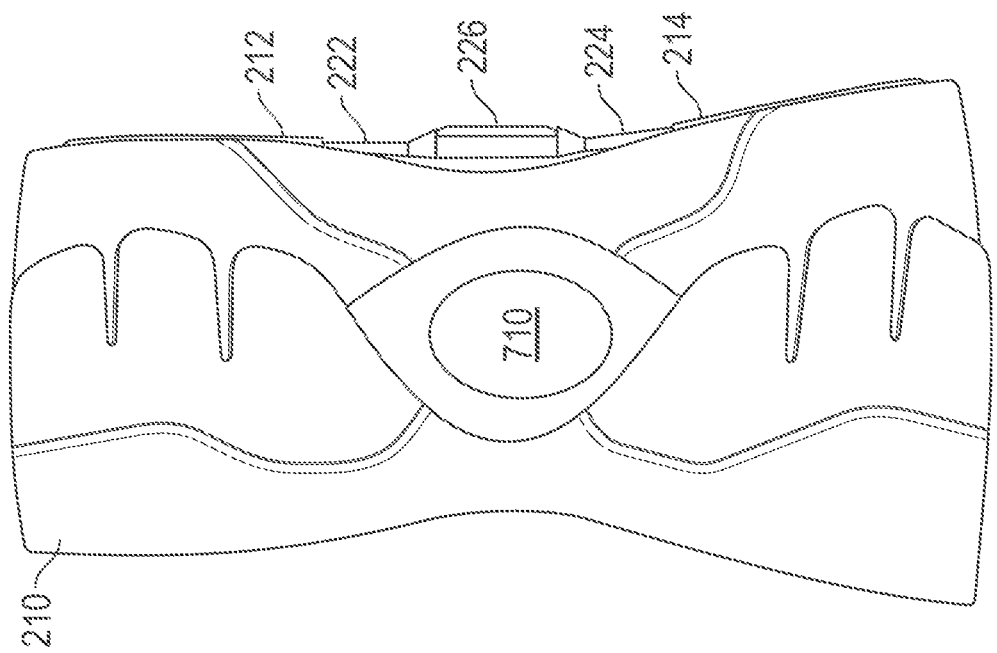
FIG. 7B illustrates the wrap of FIG. 7A in a secured orientation, in accordance with some embodiments.
Figure 7A:
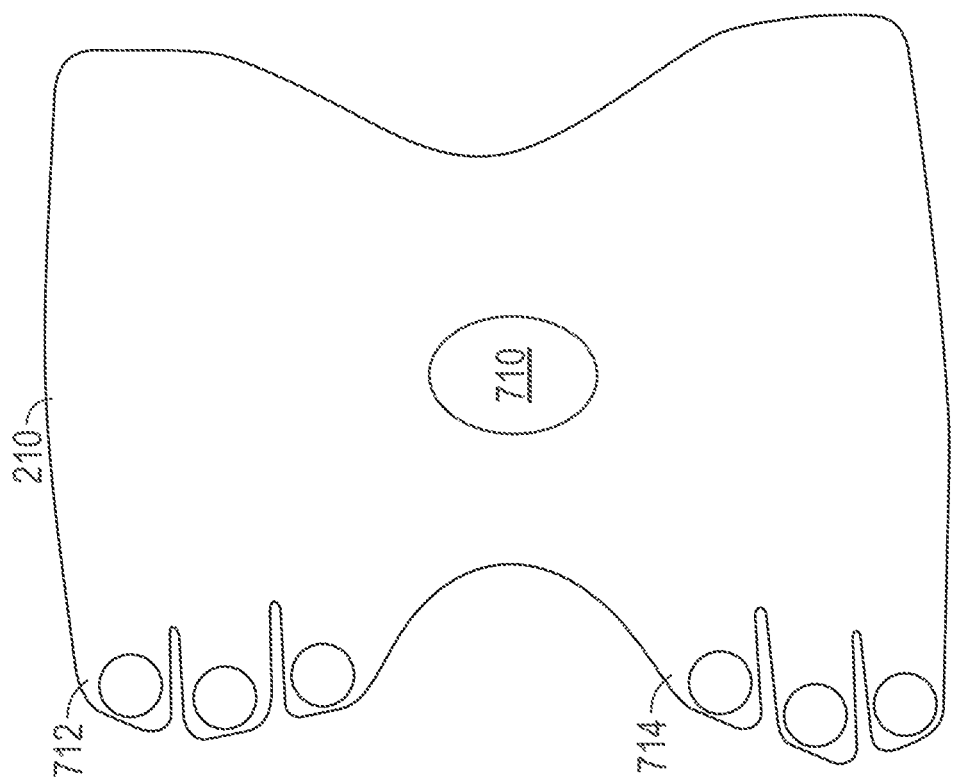
FIG. 7A illustrates a wrap of the brace of FIGS. 2A and 2B in an unsecured orientation, in accordance with some embodiments.

FIG. 7A illustrates wrap 210 of brace 200 of FIGS. 2A and 2B in an unsecured orientation, in accordance with some embodiments. Wrap 210 may comprise one or more upper fastening elements 712 configured to secure an upper portion of wrap 210 around the upper leg of the patient. Wrap 210 may further comprise one or more lower fastening elements 714 configured to secure a lower portion of wrap 210 around the lower leg of the patient. Fastening elements 712, 714 may comprise hook and loop fasteners, snaps, clips, or any other element of removably fastening wrap 210 around a limb of the patient. Wrap 210 may further comprise an opening 710 configured to align with a patella of the patient, thereby providing increased comfort as well as more stable alignment of wrap 210 with the leg of the patient. FIG. 7B illustrates wrap 210 of FIG. 7A where upper fastening elements 712 and lower fastening elements 714 have secured wrap 210 around the leg of the patient.

Figure 8B:
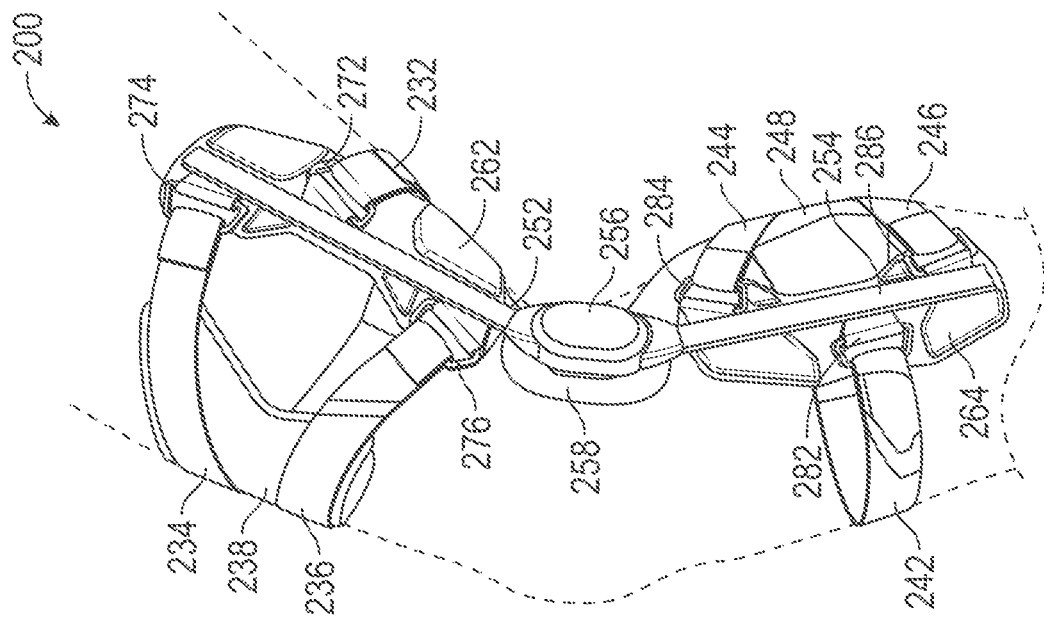
FIG. 8B illustrates a perspective view of a lateral side of the brace of FIG. 8A.
Figure 8A:
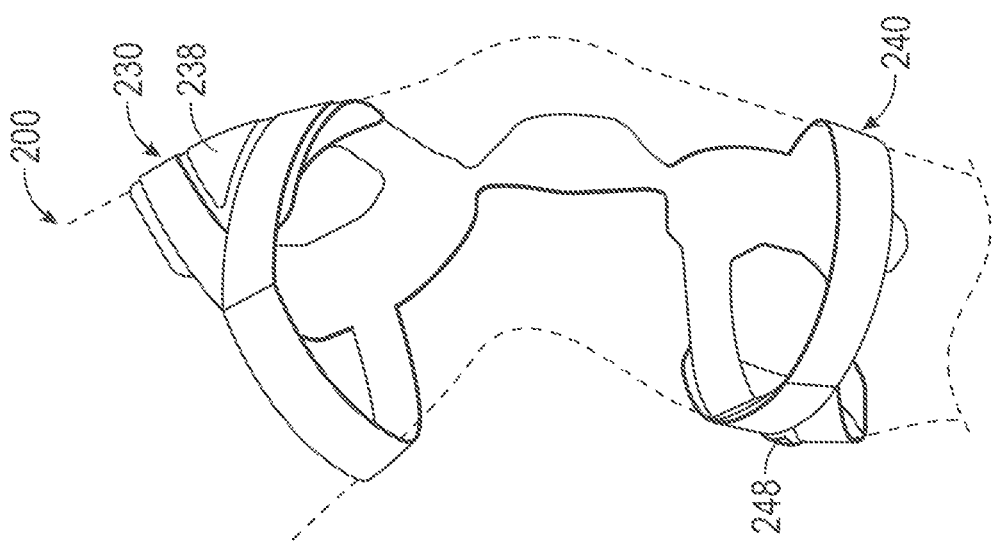
FIG. 8A illustrates a perspective view of a medial side of a brace, in accordance with some embodiments.

FIG. 8A illustrates a perspective view of a medial side of a brace 800, which is substantially identical to brace 200 without wrap 210 or first medial arm 222, second medial arm 224 and medial hinge assembly, in accordance with some embodiments. FIG. 8B illustrates a perspective view of a lateral side of brace 800 of FIG. 8A. As shown, brace 800 includes all features of brace 200 previously described except omitting wrap 210, first medial arm 222, second medial arm 224 and medial hinge assembly. All other functionality is as previously described for brace 200.

Figure 9B:
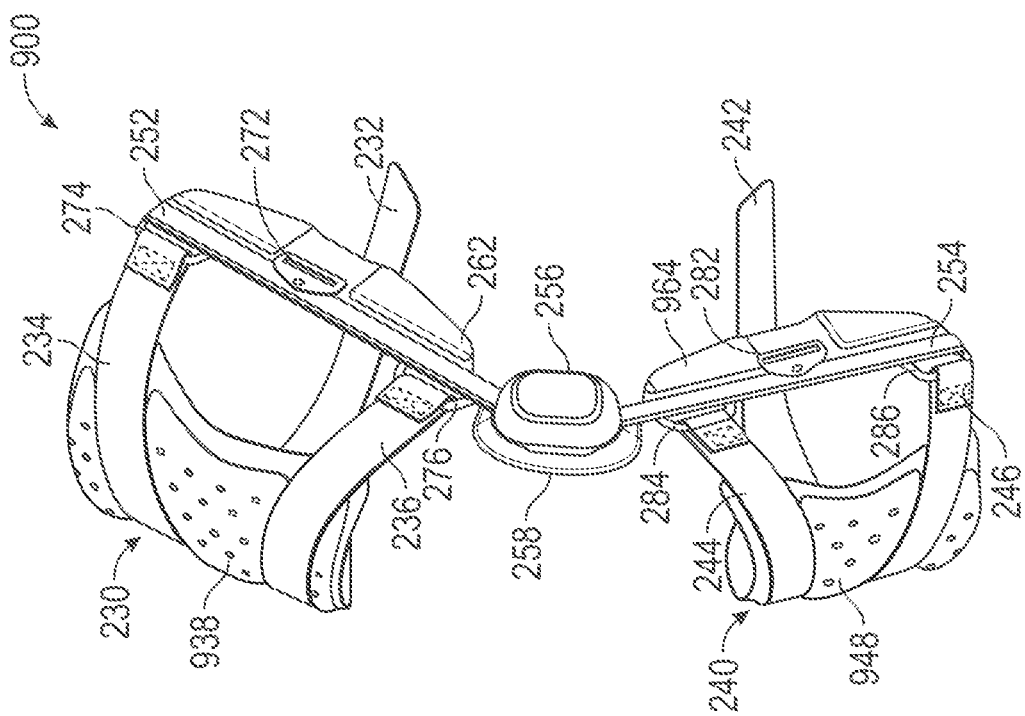
FIG. 9B illustrates a perspective view of the lateral side of the brace of FIG. 9A, further comprising a thigh pad and a shin pad, in accordance with some embodiments.
Figure 9A:
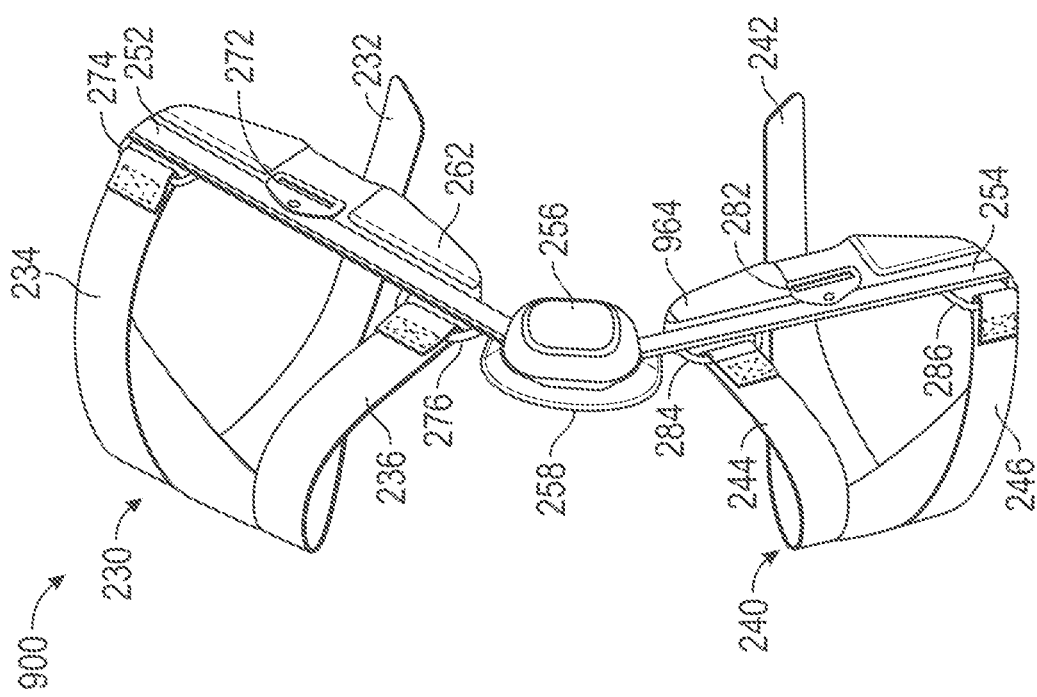
FIG. 9A illustrates a perspective view of a lateral side of a brace, in accordance with some embodiments.

FIG. 9A illustrates a perspective view of a lateral side of a brace 900, in accordance with some embodiments. As shown, brace 900 includes all features of brace 800 previously described in connection with FIGS. 8A and 8B except thigh pad 238, calf pad 248, and as further described below.

Brace 900 may comprise a lower pad 964 configured to be disposed between second lateral arm 254 and a lateral side of the patient's lower leg, in a mirror configuration to lower pad 264 as previously described in connection with FIGS. 2A and 2B. Accordingly, fastening elements 282, 284, 286 may be secured to at least one of lower pad 964 and second lateral arm 254 in a mirror configuration to that previously described in connection with FIGS. 2A and 2B. Lower pad 964 may comprise foam, rubber, an elastomer, plastic, 2#EVA, Lycra laminate, brush nylon, or any other suitable material, thermoformed or otherwise, for providing a cushion between second lateral arm 254 and the lateral side of the patient's lower leg. In some embodiments, lower pad 964 may be secured to second lateral arm 254 via any suitable method, for example, hook and loop fasteners, snaps, clips, rivets, an adhesive, etc.

Lower strap 240 is configured to secure one or more of lower pad 264 and second lateral arm 254 to the lower leg of the patient in the reverse fashion as that described in connection with FIGS. 2A and 2B. Lower strap 240 may wrap around the lower leg of the patient such that first end 242 is disposed around a posterior portion of the patient's lower leg, while second and third ends 244, 246 are disposed around an anterior portion of the patient's lower leg.

FIG. 9B illustrates a perspective view of the lateral side of brace 900 of FIG. 9A, further comprising a thigh pad 938 and a shin pad 948, in accordance with some embodiments. Thigh pad 938 is configured to be disposed between and secured in place by upper strap 230 and the thigh of the patient. Thigh pad 938 may be substantially similar to thigh pad 238 previously described in connection with FIGS. 2A and 2B.

In some embodiments, brace 200 may further comprise shin pad 948 configured to be disposed between and secured in place by lower strap 240 and the shin of the patient. Shin pad 948 may comprise foam, rubber, an elastomer, plastic, 2#EVA, Lycra laminate, brush nylon, or any other suitable material, thermoformed or otherwise, for providing a cushion between lower strap 240 and the shin of the patient.

Figure 10:
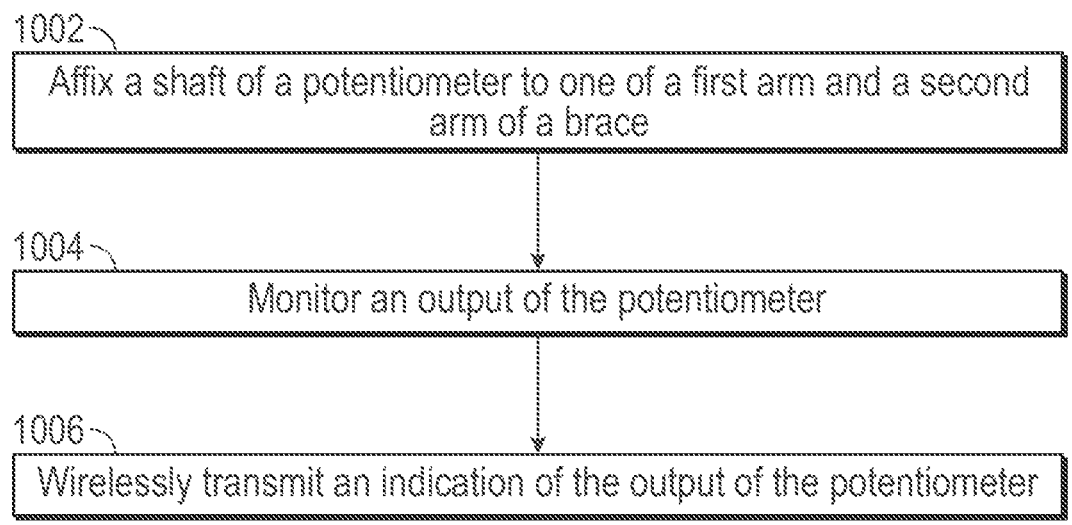
FIG. 10 illustrates a flowchart of a method of monitoring a relative angular orientation of a first arm of a brace relative to a second arm of the brace, in accordance with some embodiments.

FIG. 10 illustrates a flowchart 1000 of a method of monitoring a relative angular orientation of a first arm of a brace relative to a second arm of the brace, in accordance with some embodiments. Flowchart 1000 may apply to the utilization of any brace described in this disclosure.

Block 1002 includes affixing a shaft of a potentiometer to one of a first arm and a second arm of a brace. For example, rotatable shaft 314 of potentiometer 310 may be affixed to one of first lateral arm 252 or first medial arm 222 as previously described in connection with any prior figure. In some embodiments, rotatable shaft 314 of potentiometer 310 may alternatively be affixed to one of second lateral arm 254 or second medial arm 224 similarly to that previously described for at least first lateral arm 252 and having similar functionality.

Block 1004 includes monitoring an output of the potentiometer. For example, controller 618 (FIG. 6) or any other suitable circuit or circuitry of PCB 308 (FIG. 3) may be configured to monitor a voltage, current or resistance output from third terminal 356 (e.g., between second and third terminals 358, 356) of potentiometer 310 as previously described in connection with any previous figure.

Block 1006 includes wirelessly transmitting an indication of the output of the potentiometer. For example, as previously described in connection with FIG. 6, controller 618 may be configured to convert the voltage, current or resistance received from the output of buffer 616 into a signal indicative of a relative angular orientation between first lateral arm 252 and second lateral arm 254 of brace 200, as a function of time and based on the received voltage.

Although the present disclosure has been described in terms of certain preferred features, other features of the disclosure including variations in dimensions, configuration and materials will be apparent to those of skill in the art in view of the disclosure herein. In addition, all features detailed in connection with any one aspect herein can be readily adapted for use in other aspects herein. The use of different terms or reference numerals for similar features in different embodiments does not imply differences other than those which may be expressly set forth. Accordingly, the present disclosure is intended to be described solely by reference to the appended claims, and not limited to the preferred embodiments disclosed herein.

What is claimed is:

1. A brace configured for attachment to a joint of a patient, the brace comprising:
    a first arm having a first end and a second end;
    a second arm having a first end and a second end;
    a hinge assembly coupling the first end of the first arm with the first end of the second arm such that the first arm and the second arm are movable to different relative angular orientations, wherein the hinge assembly enables the first arm to rotate about a first axis and enables the second arm to rotate about a second axis when the first arm and the second arm are moved to different relative angular orientations relative to the hinge assembly, the first axis being in parallel with and having a spatial separation from the second axis;
    a potentiometer coupled to the hinge assembly; and
    an integrated remote patient monitoring device configured to:
        receive signals from the potentiometer indicative of the different relative angular orientations of the first arm with respect to the second arm,
        determine at least one of a range of motion, an angular velocity and an acceleration of the joint of the patient based at least in part on the signals from the potentiometer when the brace is worn by the patient, and
        wirelessly transmit at least one of an indication of the signals from the potentiometer and an indication of the determination to a communication device.

2. The brace of claim 1, wherein the spatial separation is fixed.

3. The brace of claim 2, wherein a rotatable shaft of the potentiometer is disposed to rotate about the first axis.

4. The brace of claim 3, wherein a portion of the rotatable shaft of the potentiometer is keyed and fits in a mating aperture in the first end of the first arm.

5. The brace of claim 4, comprising a second shaft, parallel to the rotatable shaft of the potentiometer, that is mechanically fixed to the rotatable shaft of the potentiometer.

6. The brace of claim 5, wherein the second shaft is disposed to rotate about the second axis.

7. The brace of claim 1, wherein the potentiometer comprises a rotatable shaft that is coupled to the first end of the first arm.

8. The brace of claim 7, wherein the rotatable shaft is coupled to have a fixed angular orientation with respect to the first end of the first arm.

9. The brace of claim 8, wherein the potentiometer comprises a resistive element, the resistive element configured to rotate with respect to the first end of the first arm.

10. The brace of claim 1, wherein the potentiometer is an analog mechanical potentiometer.

11. The brace of claim 1, wherein the potentiometer is a digital potentiometer.

12. The brace of claim 1, wherein the potentiometer is mounted to a printed circuit board.

13. The brace of claim 1, wherein an output of the potentiometer is connected to a buffer.

14. The brace of claim 1, wherein an input of the potentiometer is coupled to a battery.

* * * * *